(12) United States Patent
Nose et al.

(10) Patent No.: US 7,370,509 B2
(45) Date of Patent: May 13, 2008

(54) ENDURANCE CALCULATION DEVICE, ENDURANCE CALCULATION METHOD, AND PROGRAM

(75) Inventors: Hiroshi Nose, Azumino (JP); Hirokazu Genno, Hirakata (JP); Keiko Watanabe, Hirakata (JP)

(73) Assignees: Sanyo Electric Co., Ltd., Moriguchi (JP); Non-Profit Organization Jukunen Taiiku Daigaku Research Center, Matsumoto (JP)

( * ) Notice: Subject to any disclaimer, the term of this patent is extended or adjusted under 35 U.S.C. 154(b) by 121 days.

(21) Appl. No.: 11/307,957

(22) Filed: Feb. 28, 2006

(65) Prior Publication Data
US 2006/0236748 A1 Oct. 26, 2006

(30) Foreign Application Priority Data
Feb. 28, 2005 (JP) .............. P2005-055217

(51) Int. Cl.
*G01M 7/00* (2006.01)
(52) U.S. Cl. .................................. 73/12.04
(58) Field of Classification Search .... 73/12.01–12.09, 73/379.01–37
See application file for complete search history.

(56) References Cited

U.S. PATENT DOCUMENTS 5,125,412 A * 6/1992 Thornton ............... 600/483
5,976,083 A * 11/1999 Richardson et al. ........ 600/300
6,277,080 B1 * 8/2001 Nissila et al. ............. 600/508
6,546,336 B1 * 4/2003 Matsuoka et al. ......... 701/213
7,177,684 B1 * 2/2007 Kroll et al. ................ 607/17
2002/0013717 A1 * 1/2002 Ando et al. ................ 705/4
2005/0101461 A1 * 5/2005 Johnson ..................... 482/141
2007/0072158 A1 * 3/2007 Unuma et al. ............. 434/247

FOREIGN PATENT DOCUMENTS

JP 2004-000646 1/2004

* cited by examiner

*Primary Examiner*—Max Noori
(74) *Attorney, Agent, or Firm*—NDQ & M Watchstone LLP; Vincent M. DeLuca

(57) ABSTRACT

An endurance calculation device according to the present invention includes: an acceleration sensor measuring acceleration acting on the subject; an impulse calculation unit calculating impulse acting on the subject based on a value of the acceleration outputted from the acceleration sensor; an output unit outputting walking information, which is information prompting the subject to increase walking speed from low speed to a maximum speed; and an endurance calculation unit calculating, based on a value of the impulse calculated by the impulse calculation unit, endurance of the subject corresponding to the value of the impulse after the first walking information is outputted by the output unit.

33 Claims, 13 Drawing Sheets

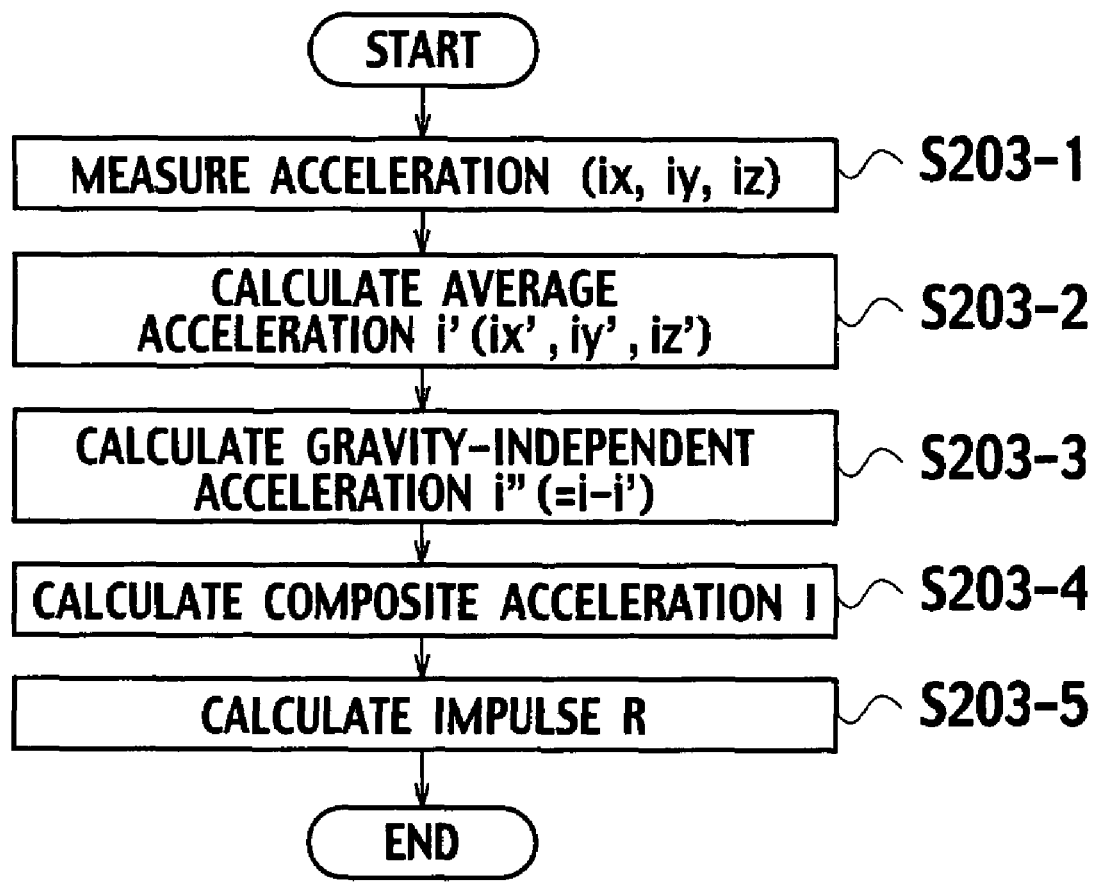

FIG. 7

| SECOND | ACCELERATION i | | | AVERAGE ACCELERATION (3 SECOND AVERAGE) i' | | | GRAVITY-INDEPENDENT ACCELERATION i''(=i-i') | | | COMPOSITE ACCELERATION i (=√((ix'')²+(iy'')²+(iz'')²) | INTEGRATION OF COMPOSITE ACCELERATION FOR FIVE SECONDS | TRANSLATION TO COMPOSITE ACCELERATION FOR ONE MINUTE |
|---|---|---|---|---|---|---|---|---|---|---|---|---|
| | ix[mG] | iy[mG] | iz[mG] | ix'[mG] | iy'[mG] | iz'[mG] | ix''[mG] (=ix-ix') | iy''[mG] (=iy-iy') | iz''[mG] (=iz-iz') | | | |
| 0.02 | 392 | 139 | 911 | | | | | | | | | |
| 0.04 | 392 | 134 | 906 | | | | | | | | | |
| 0.06 | 398 | 129 | 901 | | | | | | | | | |
| . . . | . . | . . | . . | AVERAGE OF MEASURED ACCELERATION i FOR THREE SECONDS | | | | | | | | |
| 2.94 | 228 | 123 | 958 | | | | | | | | | |
| 2.96 | 249 | 123 | 968 | | | | | | | | | |
| 2.98 | 249 | 107 | | | | | | | | | | |
| 3 | 244 | 96 | 968 | 247.8 | 132.9 | 958.7 | -3.8 | -36.8 | 9.3 | 38.2 | | |
| 3.02 | 217 | 118 | 989 | 246.6 | 132.8 | 959.2 | -29.6 | -14.8 | 29.8 | 44.5 | | |
| 3.04 | 223 | 134 | 973 | 245.5 | 132.8 | 959.7 | -22.5 | 1.2 | 13.3 | 26.2 | | |
| 3.06 | 228 | 134 | 958 | 244.4 | 132.8 | 960.1 | -16.4 | 1.2 | -2.1 | 16.6 | | |
| . . . | . . | . . | . . | . . | . . | . . | . . | . . | . . | . . | | |
| 4.98 | 201 | 188 | 958 | 214.5 | 139.0 | 968.9 | 13.1 | 33.9 | 35.0 | 50.5 | | |
| 5 | 238 | | | | | | 23.8 | 54.4 | 20.0 | 62.6 | 15648.4 | 11266834 |
| 5.02 | 244 | | | | | | 29.5 | 49.0 | -10.9 | 58.3 | | |
| . . . | . . | . . | . . | . . | . . | . . | . . | . . | . . | . . | | |
| 5.98 | 249 | 161 | 953 | 215.1 | 139.1 | 968.7 | 33.9 | 21.9 | -15.7 | 43.3 | | |
| 60 | 254 | 166 | 942 | 215.4 | 139.1 | 968.5 | 38.6 | 26.9 | -26.5 | 54.0 | 10829.9 | 129958.7 |
| . . | . . | . . | . . | . . | . . | . . | . . | . . | . . | . . | | |

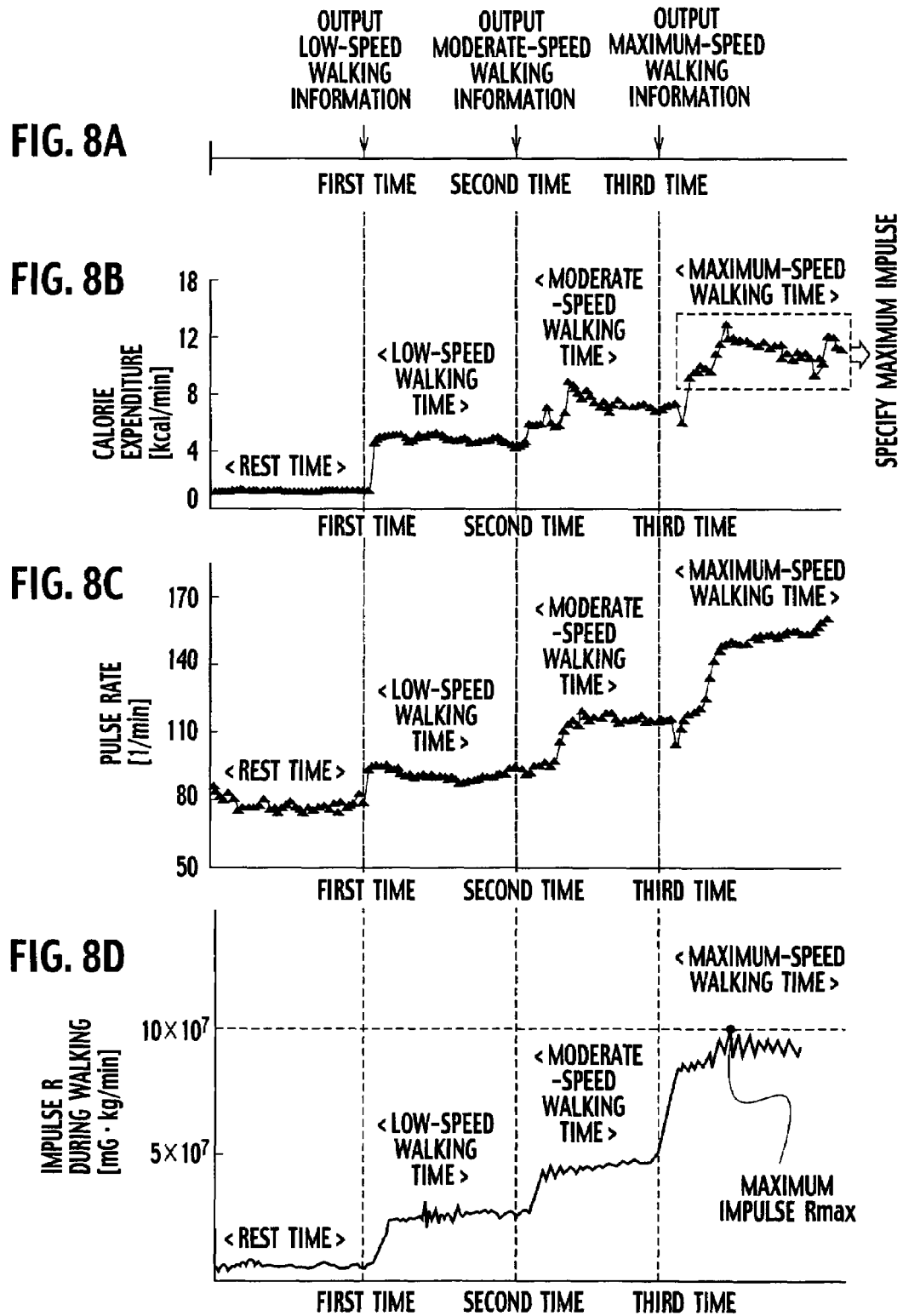

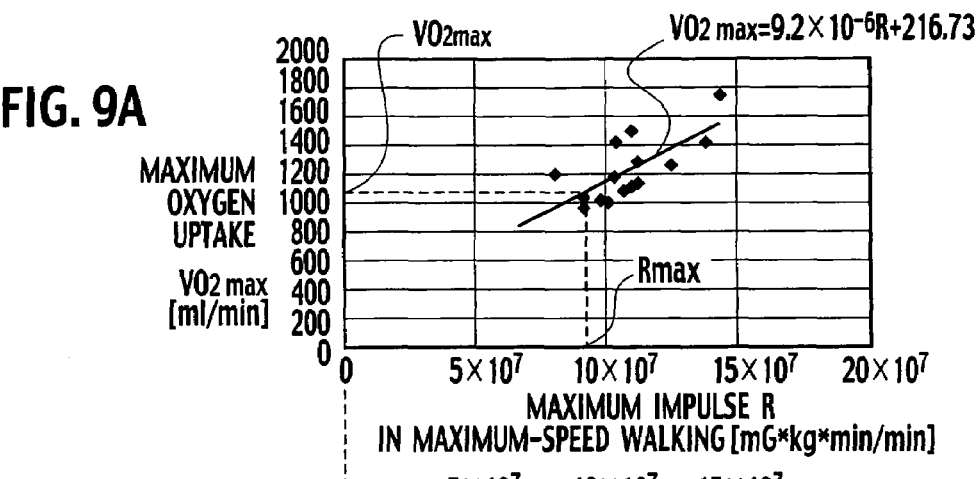
FIG. 9A
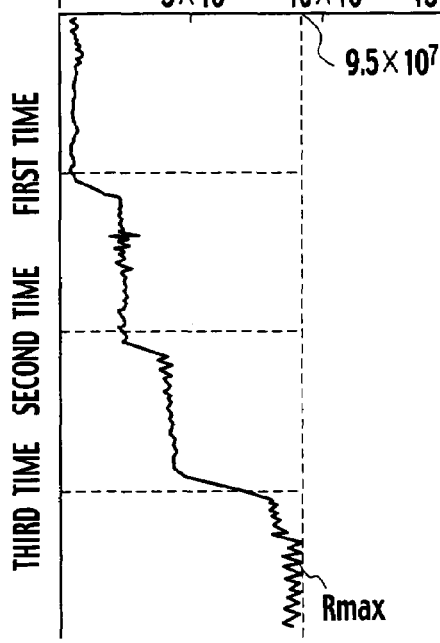
FIG. 9B
FIG. 10
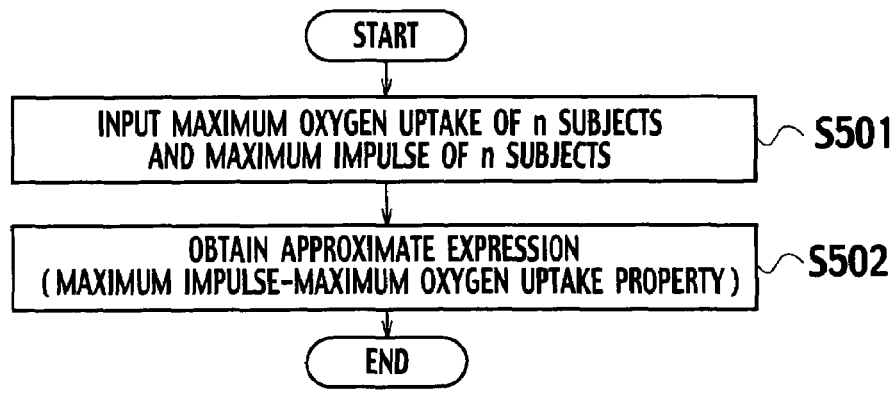

FIG. 14
| | TRAINING MODE GROUP (44 SUBJECTS) | NORMAL WALKING GROUP (54 SUBJECTS) | DO NOTHING GROUP (44 SUBJECTS) |
|---|---|---|---|
| AGE | 65.2±5.8 | 63.1±5.1 | 62.6±6.4 |
| HEIGHT (cm) | 157.5±8.3 | 156.5±7.4 | 154.5±5.3 |
| WEIGHT (kg) | 57.8±8.3 | 55.7±7.4 | 55.4±7.3 |
| BMI (kg/m$^2$) | 23.2±2.4 | 22.7±2.5 | 23.1±1.5 |
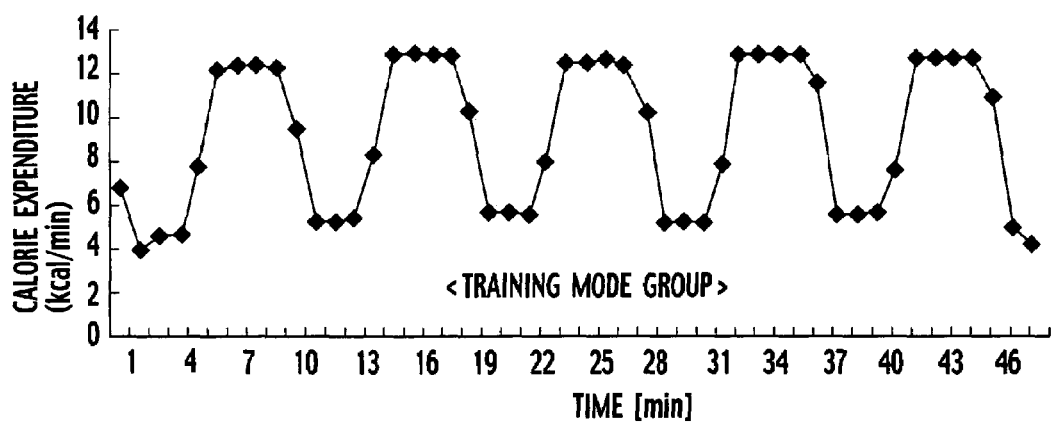
FIG. 15A
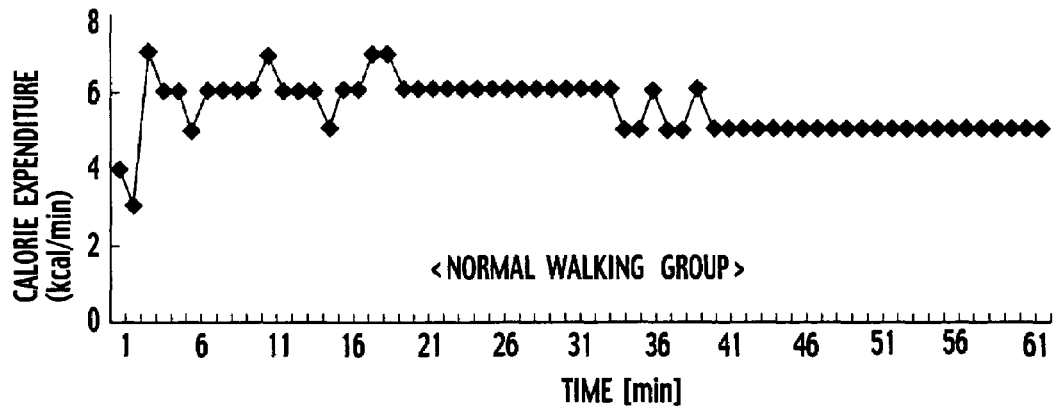
FIG. 15B

ENDURANCE CALCULATION DEVICE, ENDURANCE CALCULATION METHOD, AND PROGRAM

CROSS REFERENCE TO RELATED APPLICATIONS

This application is based upon and claims the benefit of priority from the prior Japanese Patent Application No. P2005-055217, filed on Feb. 28, 2005; the entire contents of which are incorporated herein by reference.

BACKGROUND OF THE INVENTION

1. Field of the Invention

The present invention relates to an endurance calculation device which is detachably worn by a subject and calculates endurance of the subject, an endurance calculation method, and a program.

2. Description of the Related Art

As a technique of calculating endurance of a subject, exercise equipment such as a treadmill or an ergometer has hitherto been proposed (for example, see Japanese Patent Laid-open Publication No. 2004-646). This exercise equipment calculates endurance of the subject by sequentially giving loads to the subject and measuring oxygen uptake or heart rate of the subject at a maximum load.

For example, the treadmill is provided with a rotating belt. The subject walks on the rotating belt rotating at low speed at an initial phase. The speed of the rotating belt is increased stepwise to the fastest limit that the subject can walk. Thereafter, when the subject reaches the physical limit, the maximum oxygen uptake or heart rate of the subject is measured to calculate the endurance of the subject.

BRIEF SUMMARY OF THE INVENTION

However, the exercise equipment such as the treadmill or ergometer is large-scale and expensive. Accordingly, it was difficult for the subject to easily know his/her own endurance with this exercise equipment.

On the other hand, there is a simple method which calculates the endurance of the subject using a step stool and not using the aforementioned equipment. In this method, the subject repeatedly steps up and down on the step stool, and when the subject is pushed to the physical limit, the pulse rate of the subject is measured. The endurance of the subject is calculated based on the pulse rate. In another method, the subject runs for a predetermined period of time, and the distance the subject has run is measured. The endurance of the subject is then calculated based on the measured distance.

However, in any of the above methods, a load continues to be applied to the subject until the subject is pushed to his/her own physical limit. A heavy burden is therefore placed on the subject, and it is difficult particularly for persons of low physical strength including elderly persons to periodically know their own endurance.

The endurance of the subject can be calculated without the above exercise equipment by measuring the distance which the subject has run for a predetermined period of time as described in the above another method. However, the predetermined period of time when the subject has run and the running distance needs to be measured. Accordingly, it takes a lot of time and effort to calculate the endurance of the subject after starting the measurement of the running distance.

The present invention was made in the light of the above points, and an object of the present invention is to provide an endurance calculation device, an endurance calculation method, and a program capable of easily calculating endurance of a subject without placing a heavy burden on the subject.

In order to solve the aforementioned problems, the present invention includes the following aspects. A first aspect of the present invention is an endurance calculation device detachably worn by a subject, including: an acceleration sensor measuring acceleration acting on the subject; an impulse calculation unit calculating impulse acting on the subject based on a value of the acceleration outputted from the acceleration sensor; an output unit outputting first walking information, which is information prompting the subject to increase walking speed from low speed to a maximum speed; and an endurance calculation unit calculating based on a value of the impulse calculated by the impulse calculation unit, endurance of the subject corresponding to the value of the impulse after the first walking information is outputted by the output unit. Any of the endurance calculation device, endurance calculation method, program provides the same operations and effects shown below.

According to the first aspect, the first walking information is outputted, and then the endurance of the subject corresponding to the maximum value of the impulse is calculated based on a maximum value of the impulse of the subject.

Accordingly, the endurance of the subject can be calculated by only the subject walking as fast as possible. The subject can therefore easily know the endurance of the subject without using exercise equipment which places a heavy burden on the subject to calculate the endurance of the subject, such as an ergometer.

Moreover, the subject can complete the preparation for calculating the endurance of the subject by only wearing the endurance calculation device. The subject can therefore easily know the endurance of the subject with minimal time and effort to prepare the calculation of the endurance of the subject.

A second aspect of the present invention is characterized in that the output unit alternately outputs second walking information and third walking information at predetermined timing. The second walking information is information prompting the subject to walk at normal speed. The third walking information is information prompting the subject to walk faster than the normal speed.

A third aspect of the present invention is that the endurance calculation device further includes a reference value setting unit setting a first reference value to a certain proportion of a maximum value of the impulse calculated by the impulse calculation unit. Moreover, the output unit outputs physical information representing information related to physical parameters of the subject when the value of the impulse calculated by the impulse calculation unit is larger than the first reference value.

Preferably, the physical information is one of either proper information or improper information. The proper information indicates that a load being applied to the subject is physically proper for the subject. The improper information indicates that the load being applied to the subject is not physically proper for the subject.

A fourth aspect of the present invention is that the reference value setting unit sets a second reference value to the maximum value of the impulse calculated by the impulse calculation unit; and the output unit outputs the proper information when the value of the impulse calculated by the impulse calculation unit is larger than the first reference value and outputs the improper information when the value of impulse is larger than the second reference value.

A fifth aspect of the present invention is that the endurance calculation device includes a reference value change unit changing, when the value of the impulse calculated by the impulse calculation unit is larger than the first reference value (or the second reference value), the first reference value (or the second reference value) according to a difference between the value of the impulse and the first reference value (or the second reference value).

A sixth aspect of the present invention is that the endurance calculation device further includes a measurement unit measuring exercise intensity representing an intensity of exercise when the subject is walking. Moreover, based on a value of the impulse acting on the subject when the exercise intensity measured by the measurement unit is maximized, the endurance calculation unit calculates the endurance of the subject corresponding to the value of the impulse.

A seventh aspect of the present invention is that the endurance calculation device includes: a measurement unit measuring exercise intensity representing an intensity of exercise when the subject is walking. Moreover, based on a value of the impulse when the exercise intensity measured by the measurement unit continues to be higher than a predetermined value for a predetermined period of time, the endurance calculation unit calculates the endurance of the subject corresponding to the value of the impulse.

An eighth aspect of the present invention is that the exercise intensity includes one or more of either pulse rate, heart rate, or calorie expenditure of the subject.

A ninth aspect of the present invention is that, when the value of the impulse calculated by the impulse calculation unit is higher than a predetermined value and maintained constant for a predetermined period of time, the endurance calculation unit calculates the endurance of the subject corresponding to the value of the impulse.

The endurance calculation device may include a reference value change unit which changes the reference value, when the pulse rate or calorie expenditure is higher than a predetermined value, according to a difference between the pulse rate or calorie expenditure and the predetermined value.

After the walking information is outputted by the output unit, the endurance calculation unit may calculate, based on a value of the impulse when the pulse rate, heart rate, or calorie expenditure of the subject is maximized, the endurance of the subject corresponding to the value of the impulse.

BRIEF DESCRIPTION OF DRAWINGS

FIG. 6 is a flowchart showing an impulse calculation process according to the embodiment.

FIG. 7 is a table showing acceleration, average acceleration, gravity-independent acceleration, and composite acceleration according to the embodiment.

FIGS. 8A to 8D are views showing calorie expenditure, pulse rate, and impulse at each time according to the embodiment.

FIGS. 9A and 9B are graphs showing maximum oxygen uptake with respect to maximum impulse according to the embodiment.

FIG. 10 is a maximum impulse-maximum oxygen uptake calculation process according to the embodiment.

FIG. 14 is a table showing a subject list according to the embodiment.

FIGS. 15A and 15B are graphs showing calorie expenditure with respect to time according to the embodiment.

DETAILED DESCRIPTION OF THE INVENTION

External View of Endurance Calculation Device

Figure 1A:
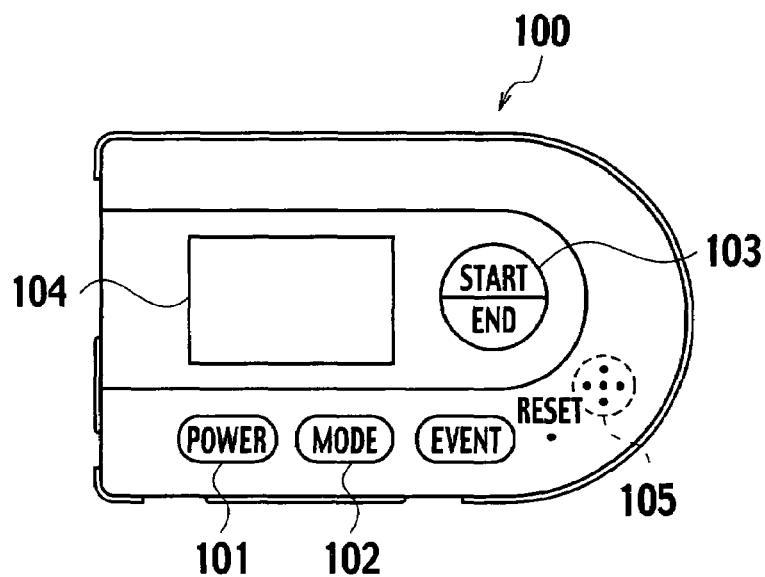
FIGS. 1A and 1B are external views showing an endurance calculation device according to an embodiment.
Figure 1B:
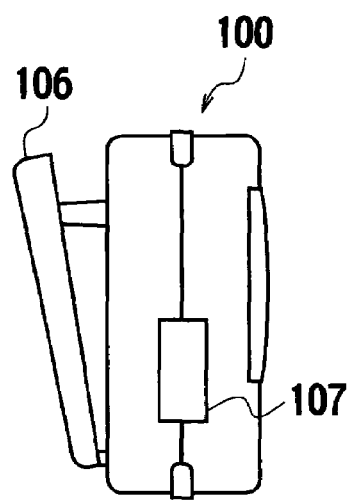

A description is given of an embodiment with reference to the drawings. FIGS. 1A and 1B are views showing an appearance of an endurance calculation device 100 according to the embodiment. FIGS. 1A and 1B are views showing a front face and a side face of the endurance calculation device 100, respectively.

The endurance calculation device. 100 is detachably worn by a subject. The endurance calculation device 100 measures quantities of exercise of the subject wearing the endurance calculation device 100, such as the number of steps, calorie expenditure, and endurance.

As shown in FIG. 1A, in the front face of the leg strength calculation device 100, a power button 101, a mode change button 102, a start button 103, a display unit 104, and a speaker 105 are provided.

The power button 101 is used to turn the endurance calculation device 100 on and off. The mode change button 102 is used to shift the endurance calculation device 100 into any one of modes including a mode to calculate the endurance of the subject (hereinafter, just referred to as an endurance mode) and a mode to cause the subject to execute an exercise according to physical strength of the subject (hereinafter, just referred to as a training mode).

The start button 103 is used to input start and stop of measurements of the quantities of exercise. The display unit 104 displays the quantities of exercise such as the measured number of steps, endurance, and calorie expenditure. The speaker 105 outputs a sound (walking information) to change walking speed of the subject.

As shown in FIG. 1B, a clip 106 with which the endurance calculation device 100 is worn on clothes of the subject is provided in a rear face of the endurance calculation device 100. A communication port 107, which can be connected to a personal computer and the like, is provided in the side face of the endurance calculation device 100.

Figure 2A:
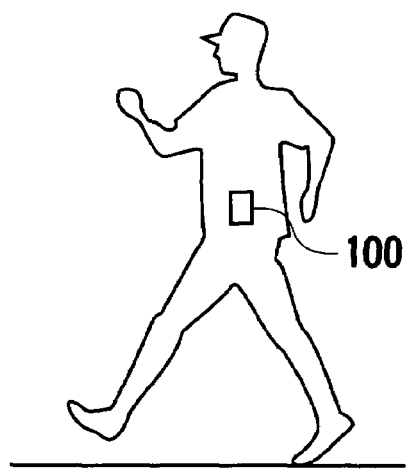
FIGS. 2A and 2B are views showing directions of accelerations acting on the endurance calculation device according to the embodiment.
Figure 2B:
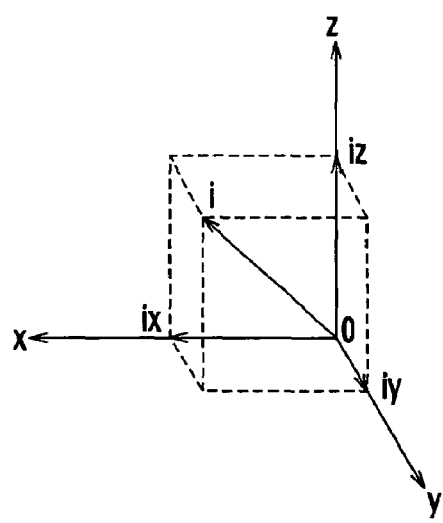

FIG. 2A is a view showing the endurance calculation device 100 of this embodiment worn by the subject. FIG. 2B is a view showing directions of accelerations acting on the subject.

As shown in FIG. 2A, the endurance calculation device 100 is worn on a subject's body or the like. As shown in FIG. 2B, when the endurance calculation device 100 is worn by the subject, accelerations act on the endurance calculation device 100 in directions of three axes orthogonal to each other. Specifically, accelerations act on the endurance calculation device 100 in directions of an axis x (herein, an axis in a direction that the subject advances), an axis y (herein, an axis in a lateral direction of the subject), and an axis z (herein, an axis in a vertical direction).

Internal Block Structure of Endurance Calculation Device

Figure 3:
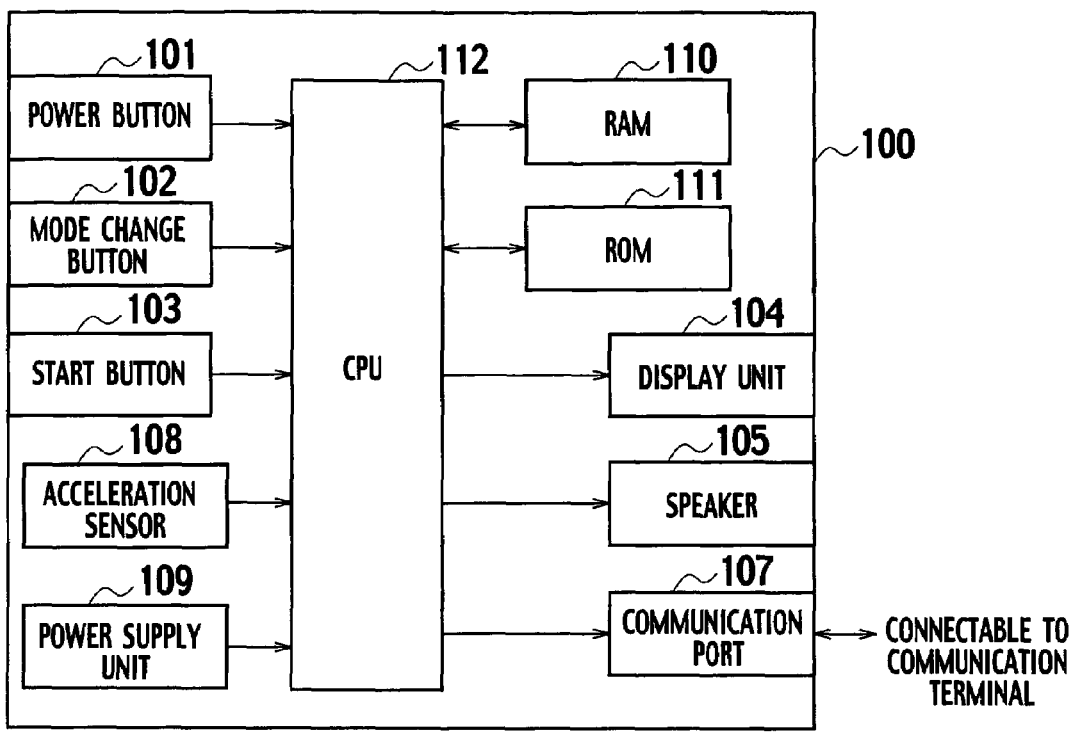
FIG. 3 is a block diagram showing an internal structure of the endurance calculation device according to the embodiment.

Next, referring to FIG. 3, a description is given of an internal block structure of the endurance calculation device. FIG. 3 is a diagram showing the internal block structure of the endurance calculation device 100 of this embodiment.

As shown in FIG. 3, the endurance calculation device 100 includes the power button 101, the mode change button 102, the start button 103, the display unit 104, the speaker 105, the communication port 107, an acceleration sensor 108, a power supply unit 109, a RAM 110, a ROM 111, and a CPU 112.

The power button 101, mode change button 102, start button 103, display unit 104, and speaker 105 are used as interfaces between the endurance calculation device 100 and the subject as described above.

The communication port 107 is a communication interface allowing the endurance calculation device 100 to be connected to a personal computer and the like. Examples of the communication port 107 include the Universal Serial Bus (USB). The personal computer connected through the communication port 107 can perform reception of measurement data of the quantities of exercise stored in the RAM 110, update of a program stored in the RAM 110 to execute an internal operation of the endurance calculation device 100, and the like.

The acceleration sensor 108 measures accelerations acting on the subject. In this embodiment, the acceleration sensor 108 measures accelerations of the subject in the directions of the three axes orthogonal to each other. Specifically, the acceleration sensor 108 measures accelerations ix, iy, and iz of the subject, respectively, acting in the directions of the axes x, y, and z.

The power supply unit 109 supplies power to operate the internal blocks. The RAM 110 temporarily stores data processed by the CPU 112. The ROM 111 stores a program to operate the internal blocks and the like.

The CPU 112 calculates impulse acting on the subject based on values of the accelerations outputted by the acceleration sensor 108. The CUP 112 constitutes an impulse calculation unit.

The CPU 112 causes the speaker 105 to output first walking information (maximum-speed walking information described later). The first walking information is information prompting the subject to increase walking speed from low speed to a maximum speed. The maximum speed is speed at when the subject is autonomously walking at maximum speed. The CPU 112 then specifies a maximum value of the calculated impulse (hereinafter, just referred to as maximum impulse).

The CPU 112 calculates, based on the specified maximum value of the impulse, endurance of the subject corresponding to the maximum value of the impulse (see a later-described endurance mode process shown in FIG. 5). The CPU 112 constitutes an endurance calculation unit.

The CPU 112 causes the speaker 105 (or the display unit 104) to alternately output second walking information (low-speed walking information later described) and third walking information (training high-speed walking information later described) at each predetermined time. The second walking information is information prompting the subject to walk at normal speed. The normal speed includes minimum speed at which the subject walks most slowly, low speed which is faster than the minimum speed, moderate speed which is faster than the low speed, and the like. The third walking information is information prompting the subject to walk at speed faster than the normal speed (see a later-described training mode process shown in FIG. 11).

Furthermore, the CPU 112 sets the value of the maximum impulse as a reference value and causes the speaker 105 (or the display unit 104) to output physical information when the calculated value of the impulse is larger than the reference value. The physical information represents information related to the subject's physical parameters. In this embodiment, the CPU 112 causes the speaker 105 (or the display unit 104) to output a warning sound (improper information). The warning sound indicates that the load on the subject is not physically proper for the subject.

On the other hand, when the calculated value of the impulse is not larger than the reference value, the CPU 112 causes the speaker 105 (or the display unit 104) to output a cheering sound (proper information). The cheering sound indicates that the load on the subject is physically proper for the subject (see a later-described particular sound output process shown in FIG. 12).

When the calculated value of the impulse is larger than the reference value, the CPU 112 may change the reference value according to a difference between the calculated value of the impulse and the reference value.

Endurance Calculation Method

Figure 4:
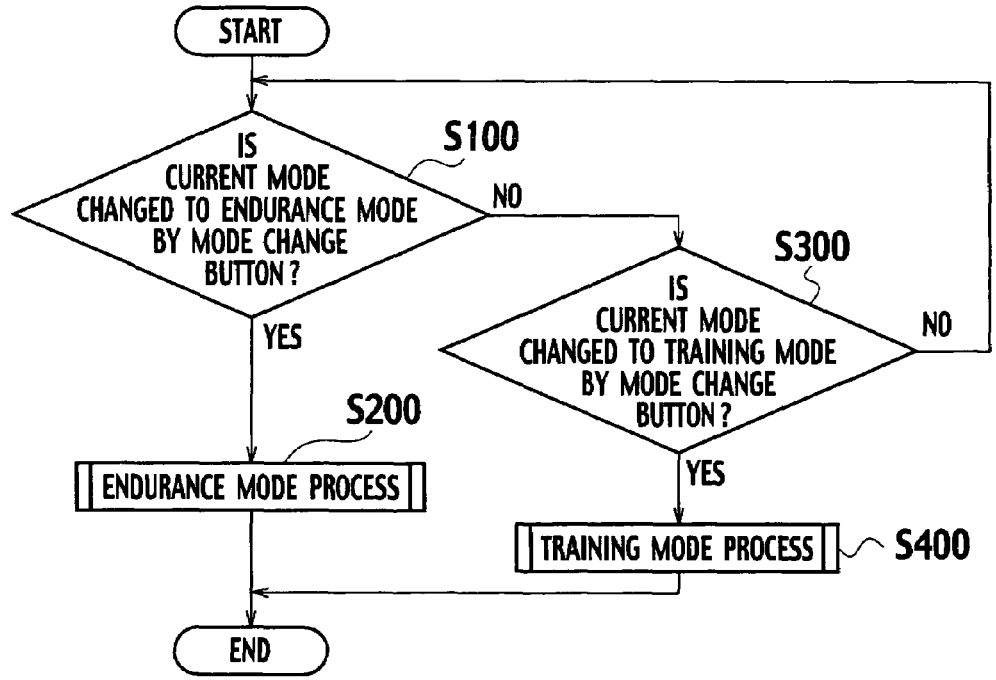
FIG. 4 is a flowchart showing an endurance calculation method according to the embodiment.

Next, a description is given of an endurance calculation method as an operation of the endurance calculation device 100 with reference to FIGS. 4 to 13. FIG. 4 is a flowchart showing the endurance calculation method. Specifically, FIG. 4 shows a concrete process executed by the endurance calculation device 100 in a mode changed by the mode change button 102.

As shown in FIG. 4, in S100, the endurance calculation device 100 judges whether a current mode is changed to the endurance mode by the mode change button 102. The endurance calculation device 100 proceeds to a process of S200 when the judgment is YES and proceeds to a process of S300 when the judgment is NO.

In S200, the endurance calculation device 100 executes the endurance mode process to calculate the endurance of the subject. This endurance mode process is described in detail with FIG. 5 described later.

In S300, the endurance calculation device 100 judges whether the current mode is changed to the training mode by the mode change button 102. The endurance calculation device 100 proceeds to a process of S400 when the judgment is YES and proceeds to the process of S100 when the judgment is NO.

In S400, the endurance calculation device 100 executes the training mode process to cause the subject to execute an exercise according to the physical strength of the subject.

The training mode process is described in detail with FIG. 11 described later. Hereinafter, a description is given of the endurance mode process of S200 and the training mode process of S400 in this order.

(1) Endurance Mode Process

Figure 5:
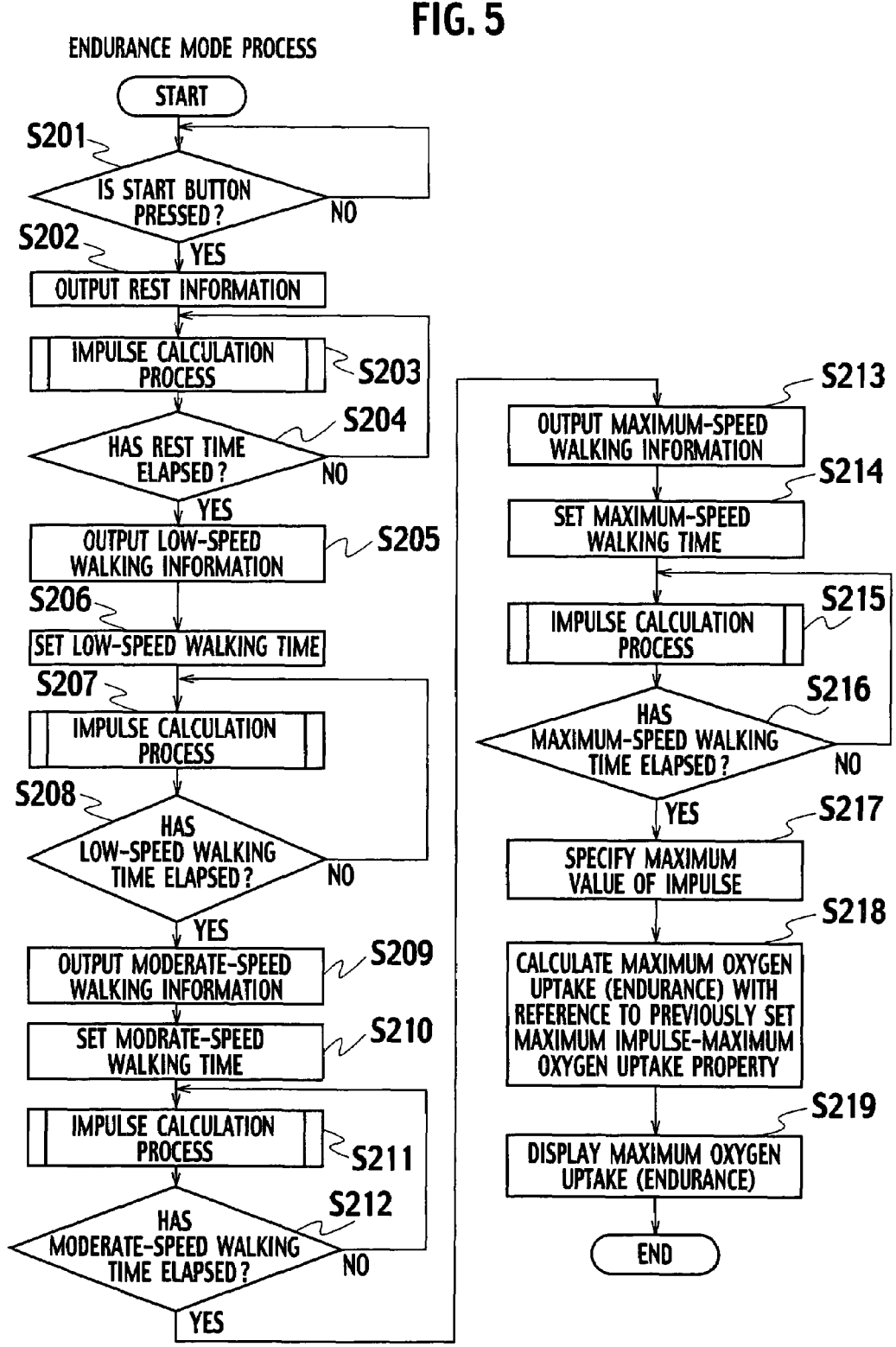
FIG. 5 is a flowchart showing an endurance mode process according to the embodiment.

Next, referring to FIGS. 5 to 10, the endurance mode process is described. FIG. 5 is a flowchart showing the endurance mode process. The endurance calculation device 100 can calculate maximum oxygen uptake (endurance) of the subject through the endurance mode process.

As shown in FIG. 5, in S201, the endurance calculation device 100 judges whether the start button 103 is pressed down. The endurance calculation device 100 proceeds to a process of S202 when the judgment is YES and repeats this process of S201 when the judgment is NO.

In S202, the endurance calculation device 100 sets rest time representing a period of time at when the subject is at rest. The endurance calculation device 100 outputs rest information prompting the subject to be at rest.

In S203, the endurance calculation device 100 executes, based on the accelerations acting on the subject, an impulse calculation process to calculate impulse of the subject.

FIG. 6 is a flowchart showing the impulse calculation process executed in S203. As shown in FIG. 6, in S203-1, the endurance calculation device 100 causes the RAM 110 to store values of the accelerations outputted from the acceleration sensor 108. Specifically, the endurance calculation device 100 causes the RAM 110 to store values of the accelerations ix, iy, and iz of the subject, respectively, acting in the directions of the axes x, y, and z.

Herein, FIG. 7 is a table showing the values of the accelerations stored in the RAM 110 and results of various calculations. As shown in FIG. 7, for example, suppose a case where measurement time between pressing down of the start button 103 and the current time is 3 seconds and the values of the accelerations ix, iy, and iz at the current time are 244, 96, and 968, respectively.

In this case, the endurance calculation device 100 causes the RAM 110 to store these values of the accelerations (the values of the accelerations ix, iy, and iz=244, 96, and 968) so as to correspond to the measurement time of 3 seconds and the acceleration i.

In S203-2, the endurance calculation device 100 calculates average acceleration i', which is average acceleration at the current time, based on the measured values of the accelerations. Hereinafter, average accelerations acting in the directions of the axes x, y, and z are indicated by ix', iy', and iz', respectively.

In this embodiment, the endurance calculation device 100 sets the average acceleration between the current time and a predetermined period of time (herein, three seconds) before the current time. As shown in FIG. 7, for example, suppose a case where the measurement time is three seconds at the current time and values of the accelerations xi, yi, and zi at the current time are 244, 96, and 968, respectively.

In this case, the endurance calculation device 100 calculates averages of values of the accelerations (values surrounded by lines in FIG. 7) between the values of the accelerations (the accelerations ix, iy, and iz=244, 96, and 968) at the current time and values of the accelerations at about three seconds before the current time (the accelerations ix, iy, and iz=392, 139, and 911) as average acceleration i' (the average accelerations ix', iy', and iz'=247.8, 132.9, and 958.7).

In S203-3, the endurance calculation device 100 subtracts the average acceleration i' from the measured acceleration i (i-i') to eliminate a gravity element from the acceleration i and sets the result of the subtraction as gravity-independent acceleration i".

As shown in FIG. 7, for example, suppose a case where the measurement time is 3 seconds and values of the accelerations ix, iy, and iz at the current time are 244, 96, and 968, respectively and the values of the average accelerations ix', iy', and iz' are 247.8, 132.9, and 958.7, respectively.

In this case, the endurance calculation device 100 calculates [the gravity-independent accelerations ix", iy", and iz"=the accelerations ix, iy, and iz–the average accelerations ix', iy', and iz'] to obtain −3.8, −36.9, and 9.3, respectively.

In S203-4, the endurance calculation device 100 calculates composite acceleration I indicating composite acceleration acting on the subject based on the gravity-independent acceleration i". Herein, the composite acceleration I can be expressed by Equation 1 below.

$$\text{Composite Acceleration } I = \sqrt{(ix'')^2 + (iy'')^2 + (iz'')^2} \qquad \text{Equation 1}$$

In S203-5, based on the composite acceleration I, the endurance calculation device 100 calculates impulse R acting on the subject. In this embodiment, the endurance calculation device 100 integrates the composite acceleration in a predetermined interval (herein, five seconds) and translates the integrated value into an integrated value of the composite acceleration for one minute.

Herein, as shown in FIG. 7, the endurance calculation device 100 integrates the composite acceleration for the measurement time of 5 seconds and multiplies the integrated value (see a shaded area shown in FIG. 7) by 12 for translation into the integrated value of the composite acceleration for one minute. The endurance calculation device 100 multiplies the integrated value of the composite acceleration for one minute by weight of the subject to calculate the impulse of the subject. Herein, impulse R=[integrated value of composite acceleration for one minute]×subject's weight.

After completing the process of S203-5, the endurance calculation device 100 proceeds to the process of S204 shown in FIG. 5.

In S204, the endurance calculation device 100 judges whether the rest time has elapsed. The endurance calculation device 100 proceeds to a process of S205 when this judgment is YES and returns to the process of S203 when the judgment is NO.

When the judgment is NO in S204, the impulse calculation process is again executed in S203. Specifically, the acceleration i is measured, and the average acceleration i', gravity-independent acceleration i", composite acceleration I, and impulse R are calculated (see FIG. 7).

In S205, the endurance calculation device 100 causes the speaker 105 to output the low speed walking information, which is information prompting the subject to walk slowly, (for example, one beep).

In S206, the endurance calculation device 100 sets low-speed walking time representing a period of time at when the subject is caused to walk slowly.

In step S207, the endurance calculation device 100 executes the same impulse calculation process as the aforementioned process of S203.

In S208, the endurance calculation device 100 judges whether the low-speed walking time has elapsed. The endurance calculation device 100 proceeds to a process of S209 when the judgment is YES and returns to the process of S207 when the judgment is NO.

When the judgment is No in S208, the impulse calculation process is again executed in S207. Specifically, the acceleration i is measured, and the average acceleration i', gravity-independent acceleration i'', composite acceleration I, and impulse R are then calculated (see FIG. 7).

In step S209, the endurance calculation 100 causes the speaker 105 to output the moderate walking-speed information (for example, two beeps), which is information prompting the subject to autonomously walk faster than the subject in the low-speed walking time.

In S210, the endurance calculation device 100 sets moderate-speed walking time, which represents a period of time at when the subject is caused to walk faster than the walking speed of the subject in the low-speed walking time.

In S211, the endurance calculation device 100 executes the same impulse calculation process as the aforementioned process of S203.

In S212, the endurance calculation device 100 judges whether the moderate-speed walking time has elapsed. The endurance calculation device 100 proceeds to a process of S213 when the judgment is YES and returns to the process of S211 when the judgment is NO.

When the judgment is No in S212, the impulse calculation process is again executed in S211. Specifically, the acceleration i is measured, and the average acceleration i', gravity-independent acceleration i'', composite acceleration I, and impulse R are then calculated (see FIG. 7).

In S213, the endurance calculation device 100 causes the speaker 105 to output maximum-speed walking information. The maximum-speed walking information is information prompting the subject to autonomously walk at a maximum speed (for example, three beeps).

In S214, the endurance calculation device 100 sets the maximum-speed walking time, which represents a period of time when the subject is caused to walk at the maximum speed.

In S215, the endurance calculation device 100 executes the same impulse calculation process as the aforementioned process of S203.

In S216, the endurance calculation device 100 judges whether the maximum-speed walking time has elapsed. The endurance calculation device 100 proceeds to a process of S217 when the judgment is YES and returns to the process of S215 when the judgment is NO.

When the judgment is No in S216, the impulse calculation process is again executed in S215. Specifically, the acceleration i is measured, and the average acceleration i', gravity-independent acceleration i'', composite acceleration I, and impulse R are then calculated (see FIG. 7).

In S217, the endurance calculation device 100 specifies a maximum value of the impulse R referring to the calculated value of the impulse R.

In S218, the endurance calculation device 100 calculates maximum oxygen uptake (this is equivalent to the endurance) corresponding to the maximum value of the impulse R specified in S217 using a set maximum impulse-maximum oxygen uptake property (expression). The method of obtaining the maximum impulse-maximum oxygen uptake property (expression) is described in detail with FIG. 10.

In S219, the endurance calculation device 100 causes the display unit 104 to output the calculated value of the maximum oxygen uptake (endurance).

The rest time (S202), low-speed walking time (S206), moderate-speed walking time (S210), and maximum-speed walking time (S206) all may be set in S202.

Herein, FIG. 8A is a view showing the rest information, low-speed walking information, moderate-speed walking information, and maximum-speed walking information being sequentially outputted at predetermined timing. FIGS. 8B to 8D are views showing the calorie expenditure, pulse rate, and impulse of the subject with respect to the measurement time. FIG. 9A is a graph showing the set maximum impulse-maximum oxygen uptake property of the subject.

As shown in FIGS. 8A to 8D, in the rest time, the subject is at rest, and the calorie expenditure, pulse rate, and impulse R of the subject are minimized. When the low-speed walking information (herein, a beep) is outputted at a first time, the subject is prompted by the low-speed walking information to walk slowly. Accordingly, the calorie expenditure, pulse rate, and impulse R of the subject are larger than those in the rest time.

When the moderate-speed walking information (herein, beep, beep) is outputted at a second time, the subject is prompted by the moderate-speed walking information to walk faster than the subject walks in the low-speed walking time. Accordingly, the calorie expenditure, pulse rate, and impulse R of the subject become larger than those in the low-speed walking time.

When the maximum-speed walking information (herein, beep, beep, beep) is outputted at a third time, the subject is promoted by the maximum-speed walking information to walk at the maximum speed. Accordingly, the calorie expenditure, pulse rate, and impulse R of the subject are maximized.

The endurance calculation device 100 specifies maximum impulse Rmax after the third time. The endurance calculation device 100 calculates the maximum oxygen uptake corresponding to the specified maximum impulse Rmax with reference to the maximum impulse-maximum oxygen uptake property (expression) shown in FIG. 9A.

For example, suppose a case where the maximum impulse Rmax of the subject after the third time is $9.5 \times 10^7$ as shown in FIG. 9B. In this case, as shown in FIG. 9A, the endurance calculation device 100 assigns the maximum impulse Rmax ($9.5 \times 10^7$) to an approximate expression of the maximum oxygen uptake=$9.2 \times 10^{-6}$R+216.73 to calculate the maximum oxygen uptake.

FIG. 10 is a flowchart showing a process to obtain the maximum impulse-maximum oxygen uptake property used in S218 above (see FIG. 9A).

In S501, the endurance calculation device 100 prompts input of the maximum impulse Rmax of a predetermined number (n) of subjects and the maximum oxygen uptake of the predetermined number (n) of subjects when the maximum impulse Rmax is provided.

In S502, the endurance calculation device 100 obtains the approximate expression (see FIG. 9A) using the least square method based on the relationship between the inputted values of the maximum impulse of the predetermined number (n) of subjects and the values of the maximum oxygen uptake of the predetermined number (n) of subjects.

The endurance calculation device 100 previously sets the approximate expression of the maximum impulse-maximum oxygen uptake property in this embodiment. However, the endurance calculation device 100 is not limited to this and may be modified as follows.

Specifically, the endurance calculation device 100 sequentially stores the values of the maximum impulse Rmax calculated in the step S217 and the values of the maximum oxygen uptake corresponding to the values of the maximum impulse Rmax in S218. When a predetermined number of values of the maximum impulse Rmax and maximum oxygen uptake are stored for a predetermined period of time, the endurance calculation device 100 calculates an approximate expression using substantially all the stored values of the maximum impulse Rmax and maximum oxygen uptake. The set approximate expression is then replaced with the calculated approximate expression.

In this case, the endurance calculation device 100 sequentially updates the approximate expression based on a larger number of values of the maximum impulse Rmax and maximum oxygen uptake. The endurance calculation device 100 can therefore more accurately calculate the maximum oxygen uptake (endurance) corresponding to the maximum impulse Rmax of the subject using the updated approximate expression.

According to such a characteristic, the maximum-speed walking information, which is information prompting the subject to autonomously walk as fast as possible, is outputted, and then the endurance of the subject corresponding to the maximum value of the impulse is calculated based on the maximum value of the impulse of the subject.

The endurance of the subject can be therefore calculated only by the subject autonomously walking from the low speed to the maximum speed. Accordingly, the subject can easily know the endurance of the subject without exercise equipment which places a heavy burden on the subject to calculate the endurance, such as the ergometer.

The subject completes the preparation for calculating the endurance of the subject by only wearing the endurance calculation device 100. Accordingly, the subject can easily know the endurance of the subject with minimal time and effort to prepare the calculation of the endurance of the subject.

(2) Training Mode Process

Figure 11:
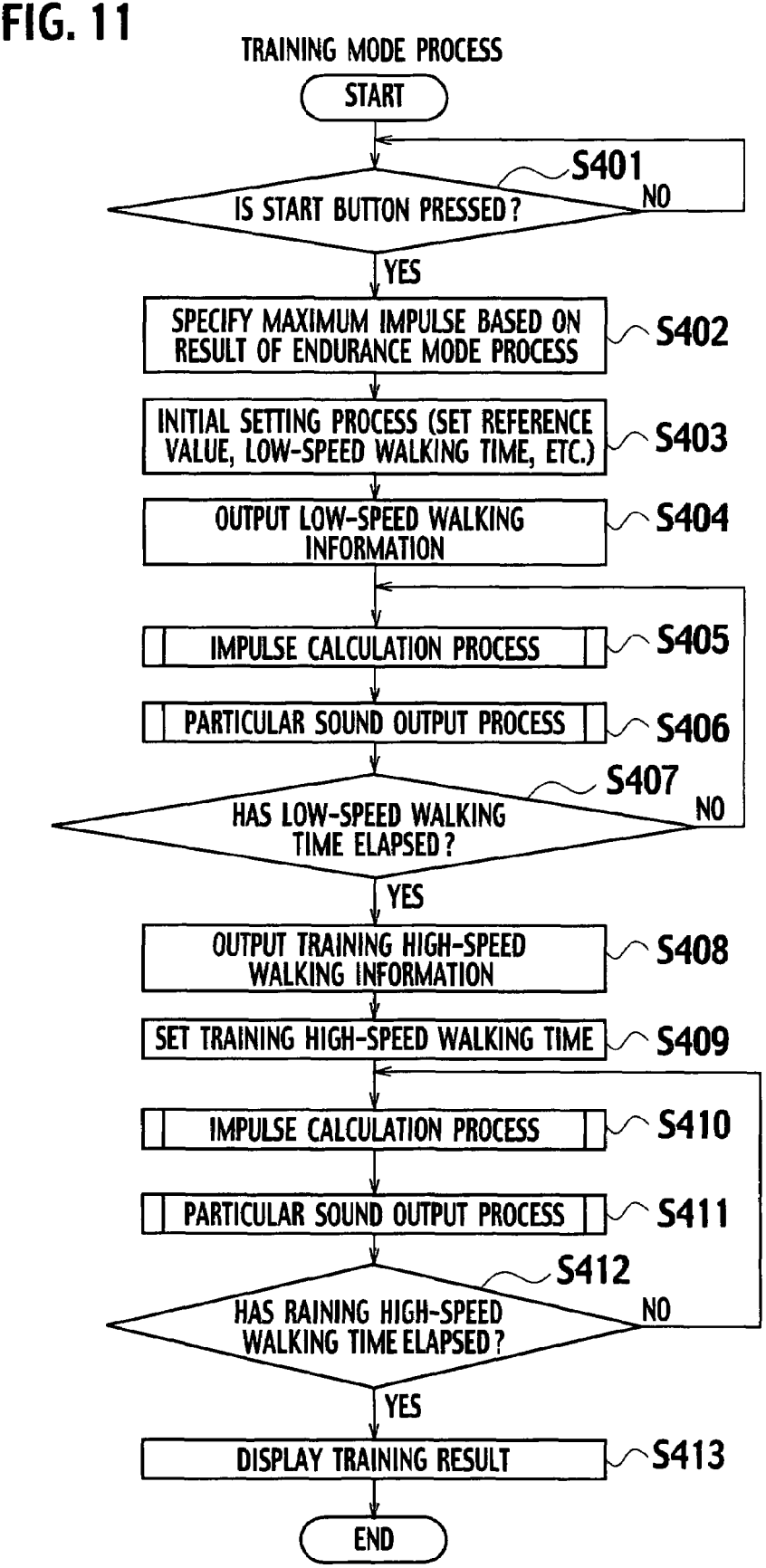
FIG. 11 is a flowchart showing a training mode process according to the embodiment.
Figure 12:
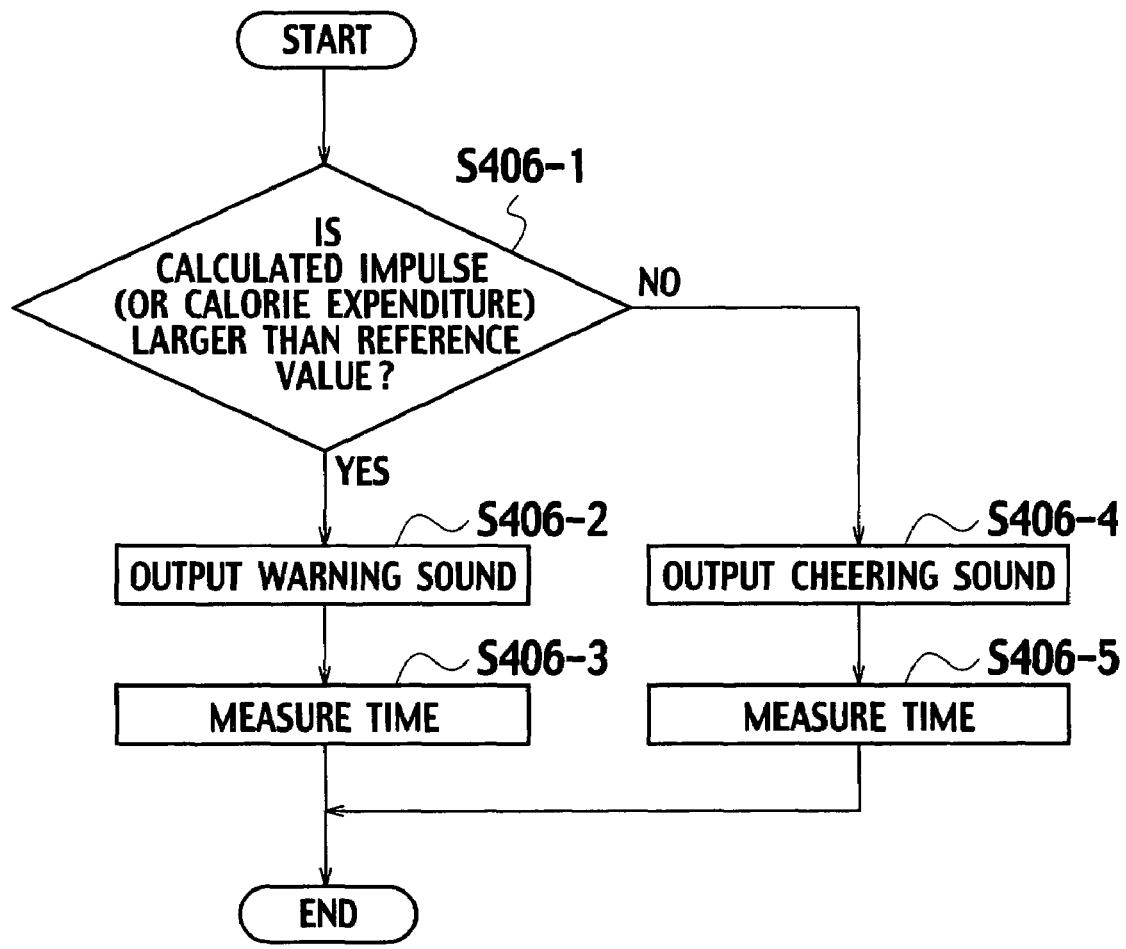
FIG. 12 is a flowchart showing a particular sound output process according to the embodiment.
Figure 13:
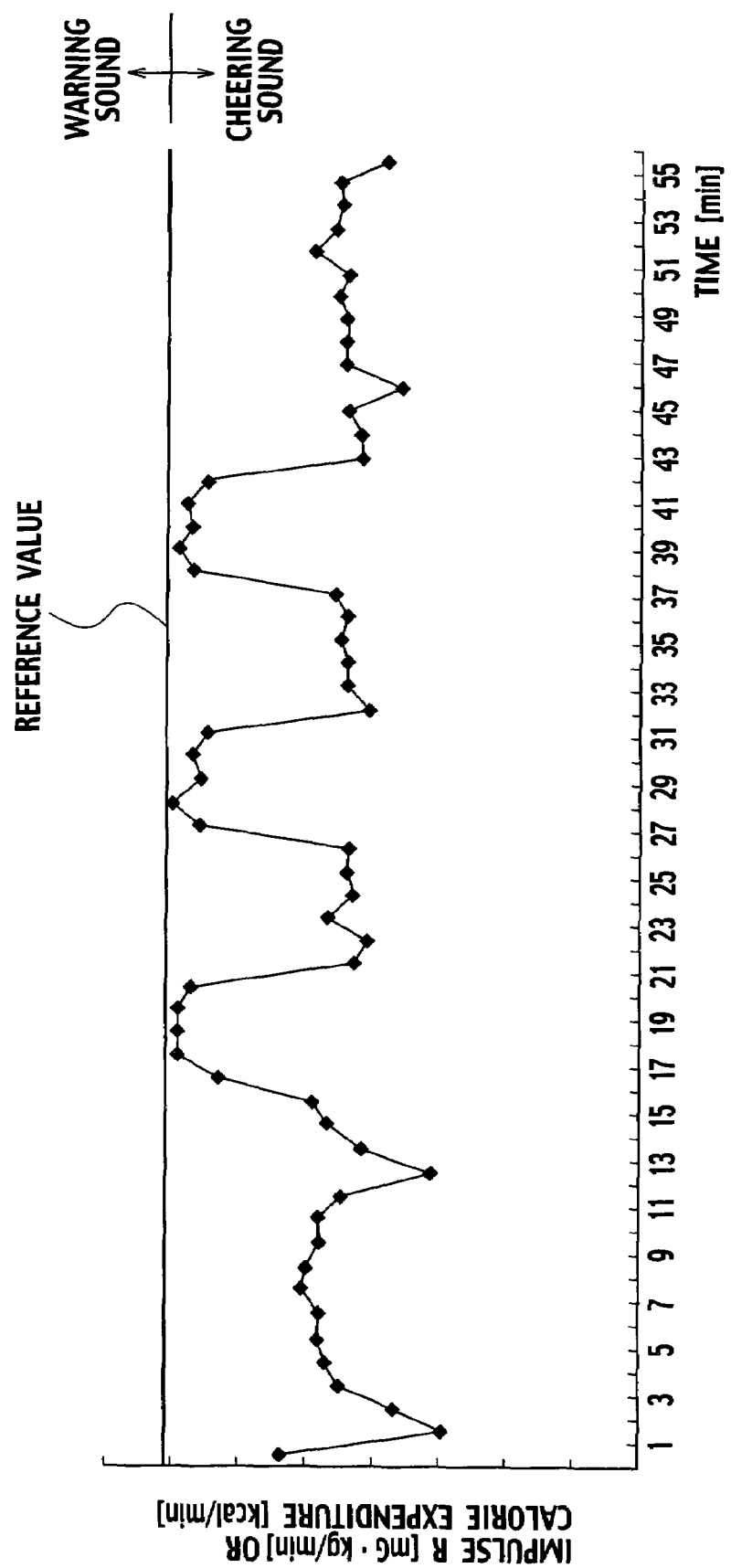
FIG. 13 is a graph showing impulse with respect to time according to the embodiment.
Figure 16:
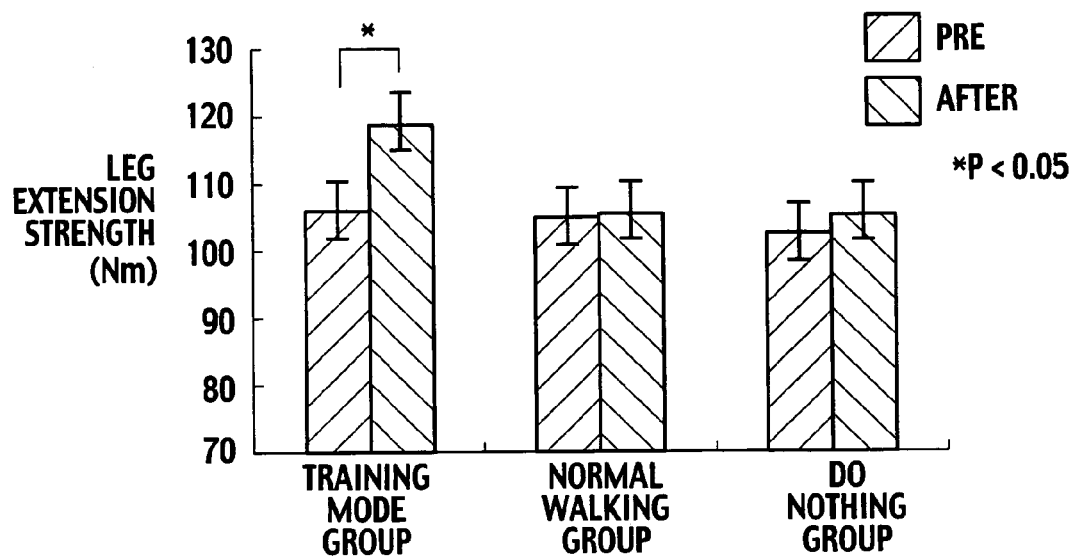
FIG. 16 is a comparative graph showing leg extension strength according to the embodiment.
Figure 17:
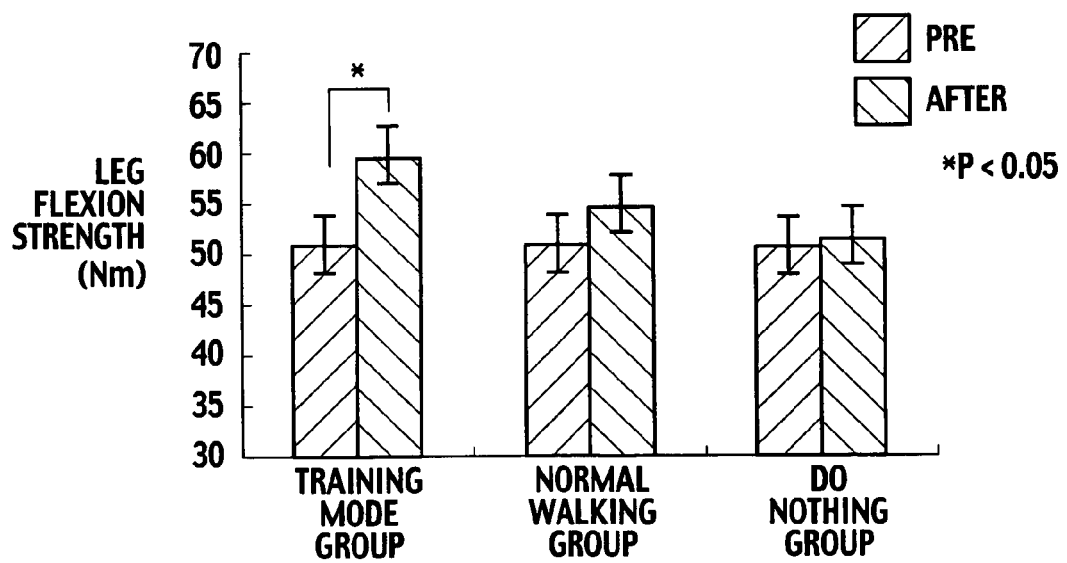
FIG. 17 is a comparative graph showing leg flexion strength according to the embodiment.
Figure 18:
FIG. 18 is a comparative graph showing maximum oxygen uptake according to the embodiment.

Next, referring to FIGS. 11 to 13, a description is given of the training mode process. The subject can more remarkably increase his/her own physical strength by this training mode process than by just walking.

As shown in FIG. 11, in S401, the endurance calculation device 100 judges whether the start button 103 is pressed down. The endurance calculation device 100 proceeds to a process of S402 when the judgment is YES and repeats this process of S401 when the judgment is NO.

In S402, the endurance calculation device 100 specifies the value of the maximum impulse calculated in the endurance mode process.

In S403, the endurance calculation device 100 sets the specified value of the maximum impulse as the reference value and sets the low-speed walking time. The low-speed walking time represents a period of time at when the subject is caused to walk at low speed.

The endurance calculation device 100 sets the reference value to the specified value of the maximum impulse but is not limited to this. For example, the endurance calculation device 100 may set the reference value to maximum calorie expenditure or maximum pulse rate of the subject.

In S404, the endurance calculation device 100 causes the speaker 105 to output the low-speed walking information, which is information prompting the subject to autonomously walk at low speed.

In S405, the endurance calculation device 100 executes the same impulse calculation process as the process of S203 above.

In S406, the endurance calculation device 100 executes a particular sound output process to output a particular sound (herein, warning or cheering sound) based on the calculated value of the impulse.

Herein, FIG. 12 is a flowchart showing the particular sound output process executed in S406. As shown in FIG. 12, in S406-1, the endurance calculation device 100 judges whether the calculated value of the impulse is larger than the reference value. The endurance calculation device 100 proceeds to a process of S406-2 when the judgment is YES and proceeds to a process of S406-4 when the judgment is NO.

In S406-2, the endurance calculation device 100 causes the speaker 105 to output the warning sound. The warning sound indicates that the load on the subject is not physically proper for the subject (see FIG. 13). In S406-3, the endurance calculation device 100 measures a period of time when the calculated value of the impulse is larger than the reference value.

In S406-4, the endurance calculation device 100 causes the speaker 105 to output the cheering sound. The cheering sound indicates that the load is physically proper for the subject (see FIG. 13). In S406-5, the endurance calculation device 100 measures a period of time when the calculated value of the impulse is not larger than the reference value.

In the particular sound output process, the endurance calculation device 100 outputs the warning or cheering sound depending on whether the calculated value of the impulse is larger than the reference value but is not limited to this. For example, the endurance calculation device 100 may output the warning or cheering sound depending on whether the pulse rate or calorie expenditure of the subject is larger than a reference value.

After completing the process of S406-5, the endurance calculation device 100 proceeds to a process of S407.

In S407, the endurance calculation device 100 judges whether the low-speed walking time has elapsed. The endurance calculation device 100 proceeds to a process of S408 when the judgment is YES and proceeds to the process of S405 when the judgment is NO.

When the judgment is NO in S407, the aforementioned impulse calculation process of S405 and particular sound output process of S406 are repeatedly executed.

In S408, the endurance calculation device 100 causes the speaker 105 to output the training high-speed walking information. The training high-speed walking information is information prompting the subject to autonomously walk faster than the normal speed during the execution of the training mode process.

In S409, the endurance calculation device 100 sets the training high-speed walking time. The training high-speed walking time represents a period of time at when the subject is caused to walk faster than the normal speed.

In S410, the endurance calculation device 100 executes the same impulse calculation process as the aforementioned process of S203.

In S411, the endurance calculation device 100 executes the same particular sound output process as the aforementioned process of S406.

In S412, the endurance calculation device 100 judges whether the training high-speed walking time has elapsed. The endurance calculation device 100 proceeds to a process of S413 when the judgment is YES and proceeds to the process of S410 when the judgment is NO. When the judgment is NO in S412, the aforementioned impulse calculation process of S410 and particular sound output process of S411 are repeatedly executed.

In S413, the endurance calculation device 100 causes the display unit 104 to display the pulse rate, calorie expenditure, accumulated time that the cheering sound has been outputted, and accumulated time when the warning sound has been outputted.

According to such a characteristic, the subject can autonomously walk at low speed by the low-speed walking information and can autonomously walk faster than the normal speed by the training high-speed walking information.

This enables the subject to alternately execute low speed walking and high speed walking (interval walking). The subject can improve the endurance, the leg strength, and the like more effectively than by executing only the low-speed walking (see FIGS. 14 to 19 later described).

Moreover, the reference value is set to the maximum value of the impulse, and the warning sound is outputted when the impulse of the subject is larger than the reference value. Accordingly, the subject can easily know that the physical strength of the subject is close to the limit and can adjust his/her own walking speed such that his/her own life cannot be threatened by exerting physical strength larger than his/her own physical limit.

Moreover, when the impulse of the subject is larger than the reference value, the warning sound is outputted. Accordingly, the subject can repeatedly execute the high-speed walking at close to his/her own physical limit and the normal walking, thus more effectively improving the endurance, the leg strength, and the like (see FIGS. 14 to 19 later described).

Furthermore, when the calculated value of the impulse of the subject is not larger than the reference value, the cheering sound is outputted. Accordingly, the subject can easily know that his/her own physical strength has not reached the limit and use as an indication of the low-speed walking.

When the calculated value of the impulse is larger than the reference value, the endurance calculation device 100 may change the reference value according to the difference between the calculated value of the impulse and the reference value. In this case, the endurance calculation device 100 changes the reference value according to the difference between the calculated value of the impulse and the reference value. Accordingly, the endurance calculation device 100 can gradually increase a level effective on the increase in physical strength of the subject and can more effectively improve the endurance, the leg strength, and the like.

Specifically, the subject repeats the low-speed walking and high-speed walking (interval walking) and executes the interval walking over the long term. The physical strength of the subject therefore gradually increases (see FIGS. 14 to 19).

Accordingly, the endurance calculation device 100 raises the reference value along with the increase in the physical strength of the subject to further increase the level effective on the increase in physical strength of the subject.

When the pulse rate or calorie expenditure of the subject is larger than a predetermined value, the endurance calculation device 100 may change the reference value according to a difference between the pulse rate or calorie expenditure and the predetermined value.

In this embodiment, the low-speed walking information and training high-speed walking information are each outputted once in the training mode process but are not limited to this. For example, the low-speed walking information and training high-speed walking information may be alternately outputted several times.

The training high-speed walking information is information prompting the subject to walk faster than the normal speed but not limited to this. For example, the training high-speed walking information may be information prompting the subject to increase walking speed from the low speed to the maximum speed.

(3) Comparison between Experimental Examples of Subjects who Executed and did not Execute Training Mode Next, referring FIGS. 14 to 19, a description is given of experimental examples of subjects who executed and did not execute the training mode.

FIG. 14 shows average ages, average heights, average weights, and average BMIs of a group of subjects who executed the training mode, a group of subjects who walked at substantially constant speed (hereinafter, just referred to as normal walking) and did not execute the training mode, and a group of subjects who did nothing.

FIG. 15A shows calorie expenditure of a subject who was executing the training mode with respect to walking time. Herein, the subject walked at low speed upon the low-speed walking information (see FIG. 11) being outputted and then walked faster than the normal speed upon the training high-speed walking information (see FIG. 11) being outputted. The drawing shows the calorie expenditure with respect to the walking time when the subject repeated the above low-speed walking and high-speed walking.

As shown in FIG. 15A, when the subject was walking at low speed, the calorie expenditure of the subject was low. When the subject was walking faster than the normal speed, the calorie expenditure of the subject was high. Accordingly, the curve of the calorie expenditure with respect to the walking time shown in FIG. 15B is wave shaped.

FIG. 15B shows calorie expenditure of a subject who was walking at substantially constant speed (normal walking) with respect to walking time. As shown in FIG. 15B, since the subject walked at substantially constant speed, the calorie of the subject was used at a substantially constant rate. Accordingly, the curve of the calorie expenditure with respect to the walking time shown in FIG. 15B is a substantially horizontal line.

Next, a comparison is made in terms of the leg extension strength, leg flexion strength, maximum oxygen uptake, systolic blood pressure, and diastolic blood pressure between the group of subjects who executed the training mode, group of subjects who executed the normal walking instead of the training mode, and group of subjects who did nothing.

Figure 19:
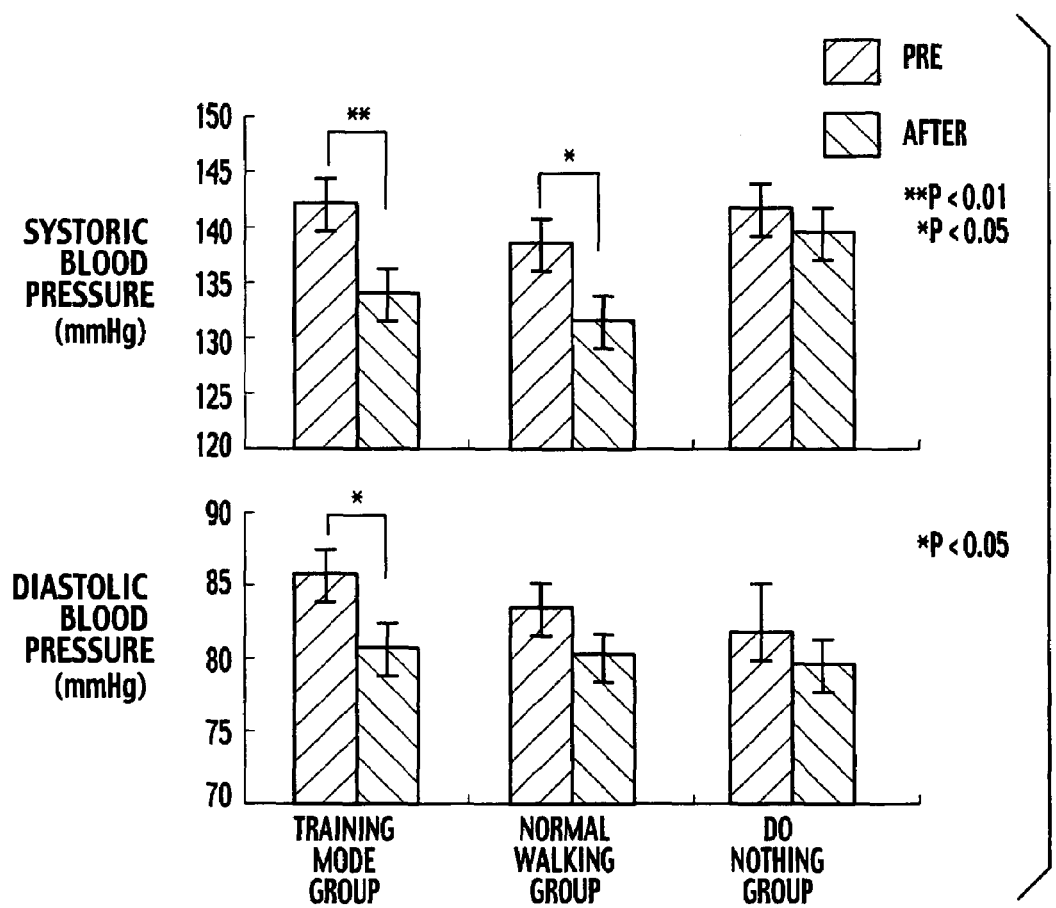
FIG. 19 is a comparative graph showing blood pressure according to the embodiment.

The group of subjects who executed the training mode produced better results than the group of subjects who executed the normal walking instead of the training mode and the group of the subjects who did nothing in terms of either the leg extension strength (FIG. 16), leg flexion strength (FIG. 17), maximum oxygen uptake (FIG. 18), systolic blood pressure (FIG. 19), and diastolic blood pressure (FIG. 19). P shown in FIGS. 16 to 19 indicates a level of significance.

Consequently, when the subject wears the endurance calculation device 100 and repeatedly executes low-speed walking and high-speed walking according to the sound outputted by the endurance calculation device 100, the subject can remarkably increase his/her own physical strength.

The endurance calculation device 100 primarily specifies the maximum value of the impulse (see S217) when causing the display unit 104 or the speaker 105 to output the maximum-speed walking information. However, the endurance calculation device 100 is not limited to this and can be modified as follows.

Specifically, the endurance calculation device 100 may measure exercise intensity representing the intensity of exercise when the subject is walking and calculate, based on the value of the impulse acting on the subject when the exercise intensity is maximum, the endurance of the subject corresponding to the value of the impulse. The exercise intensity includes one or more of either the pulse rate, heart rate, calorie expenditure, or the like of the subject.

For example, the endurance calculation device 100 specifies a value of the impulse when the measured pulse rate, heart rate, or calorie expenditure is maximized. The endurance calculation device 100 calculates, based on the specified value of the impulse, the endurance corresponding to the specified value of the impulse.

The endurance calculation device 100 may calculate, based on a value (maximum value) of the impulse when the measured exercise intensity (including one or more of either the pulse rate, heart rate, calorie expenditure, or the like of the subject) continues to be higher than a predetermined amount for a predetermined period of time, the endurance of the subject corresponding to this value of the impulse.

The predetermined amount includes the maximum value of the exercise intensity in a predetermined period of time (time of the rest time, low-speed walking time, moderate-speed walking time, or maximum-speed walking time) and the above value (substantially maximum value) of the exercise intensity in the predetermined period of time when this value of the exercise intensity is maintained for a particular duration.

Alternatively, when there are maximum values of the exercise intensity found in a plurality of phases (the rest time, low-speed walking time, moderate-walking time, and maximum-speed walking time shown in FIG. 8), the predetermined amount includes a maximum value of the exercise intensity in a final phase (the maximum-speed walking time shown in FIG. 8).

The predetermined amount or another amount certainly includes not only the aforementioned maximum values but also values around the maximum values.

When the calculated value of the impulse is larger than a predetermined value and maintained constant for a predetermined period of time, the endurance calculation device 100 may calculate the endurance of the subject corresponding to this calculated value of the impulse.

When causing the display unit 104 or speaker 105 to output the maximum-speed walking information, the endurance calculation device 100 may calculate an average of the impulse and specify a maximum value of the impulse belonging to a predetermined range around the calculated average.

The endurance calculation device 100 sets the reference value to the specified maximum value of the impulse. The endurance calculation device 100 outputs the warning sound when the current value of the impulse is larger than the reference value and outputs the cheering sound when the current impulse is not larger than the reference value (see S403 and S406). However, the endurance calculation device 100 is not limited to this and can be modified as follows.

Specifically, the endurance calculation device 100 sets a reference range to a predetermined range in the maximum value of the impulse (for example, a range of 70% or more and less than 80% of the maximum value of the impulse). The endurance calculation device 100 outputs the warning sound when the current value of the impulse is larger than the reference range (for example, 80% or more of the maximum value of the impulse) and outputs the cheering sound when the current value of the impulse is within the reference range (for example, 70% or more and less than 80% of the maximum value of the impulse).

The endurance calculation device 100 may set the reference value to a certain proportion of the specified maximum value of the impulse (for example, 70% or more of the maximum value of the impulse), measure a period of time when the calculated value of the impulse is larger than the reference value, and output the result of the measurement.

In this case, the endurance calculation device 100 measures the period of time when the impulse is larger than the reference value and outputs the measured period of time. The subject can refer to this period of time as an indication of whether to stop the current training.

The endurance calculation device 100 may change the low-speed walking time (see S403) and training high-speed walking time (see S409) depending on the magnitude of the calculated maximum oxygen uptake (see S502).

For example, the endurance calculation device 100 may set the training high-speed walking time longer in the training mode process when the maximum oxygen uptake is larger than a particular value and set the training high-speed walking time shorter in the training mode process when the maximum oxygen uptake is not larger than the particular value.

In this case, a subject whose maximum oxygen uptake is larger than the particular value has higher physical strength than a subject whose maximum oxygen uptake is not larger than the particular value. Accordingly, when the endurance calculation device 100 sets the training high-speed walking time longer in the training mode process, the subject of higher physical strength executes the high-speed walking for a longer time in the training mode and can further increase the physical strength.

On the other hand, a subject whose maximum oxygen uptake is not larger than the particular value has lower physical strength than a subject whose maximum oxygen uptake is larger than the particular value. Accordingly, if the endurance calculation device 100 sets the training high-speed walking time shorter in the training mode process, the subject of lower physical strength executes the high-speed walking for a shorter time in the training mode, and it is possible to prevent an excessive load.

In the particular sound output process, only one reference value is set, but it is possible to set a plurality of reference values. For example, the endurance calculation device 100 sets a certain proportion of the specified maximum value of the impulse as a first reference value and sets the specified maximum value of the impulse as a second reference value. The endurance calculation device 100 may output the cheering sound when the calculated value of the impulse is larger than the first reference value and output the warning sound when the calculated value of the impulse is larger than the second reference value.

In this case, the second reference value is set to the maximum value of the impulse, and the warning sound is outputted when the value of the impulse of the subject is larger than the second reference value. Accordingly, the subject can easily know that the physical strength of the subject is close to the limit and can adjust his/her walking speed so that the life of the subject cannot be threatened by exertion of physical strength larger than the physical limit of the subject.

Moreover, when the value of the impulse of the subject is larger than the first reference value, the cheering sound is outputted. The subject can therefore repeat high-speed walking (with the cheering sound) at a level effective on increasing the physical strength of the subject and the normal walking (without the cheering sound), thus more effectively improving the endurance, the leg strength, and the like (see FIGS. 14 to 19 later described).

Furthermore, when the value of the impulse of the subject is not larger than the first reference value, the cheering sound is not outputted. This allows the subject to easily know that the walking speed of the subject is slow or normal and can be an indicator of the low-speed walking.

When the value of the impulse calculated by the impulse calculation unit is larger than the second reference value, the endurance calculation device 100 may change the second reference value according to the difference between the calculated value of the impulse and the second reference value.

Program

A program operating in the above endurance calculation device has same functions as those of the above CPU 112. The program causes a computer to function as an impulse calculation unit, an output unit, an endurance calculation unit and a reference value change unit. The impulse calculation unit calculates impulse acting on a subject based on a value of acceleration outputted from the acceleration sensor. The output unit outputs first walking information, which is information prompting the subject to increase walking speed from low speed to a maximum speed. After the first walking information is outputted by the output unit, the endurance calculation unit calculates, based on the value of the impulse calculated by the impulse calculation unit, endurance of the subject corresponding to the calculate value of the impulse. When the value of the impulse calculated by the impulse calculation unit is larger than the reference value, the reference value change unit changes the reference value according to a difference between the value of the impulse and the reference value.

A dedicated program may be stored in a recording medium. This recording medium is a hard disk, a flexible disk, a compact disk, an IC chip, a cassette tape, or the like.

The above description is given of the examples of the present invention. However, the description just shows concrete examples and does not particularly limit the present invention. The design of a concrete configuration and the like of each portion can be properly changed. Moreover, the configurations of the embodiments and modifications can be properly combined. The aforementioned operations and effects of the embodiments and modifications are just most preferable operations and effects produced by the present invention, and the operations and effects of the present invention are not limited to those described in the aforementioned embodiments and modifications.

What is claimed is:

1. An endurance calculation device detachably worn by a subject, comprising:
    an acceleration sensor configured to measure acceleration acting on the subject;
    an impulse calculation unit configured to calculate an impulse acting on the subject based on a value of the acceleration outputted from the acceleration sensor;
    an output unit configured to output first walking information, which is information prompting the subject to increase walking speed from low speed to maximum speed; and
    an endurance calculation unit configured to calculate, based on a value of the impulse calculated by the impulse calculation unit, a measure of endurance of the subject after the first walking information is outputted by the output unit,
    wherein the endurance calculation unit calculates maximum oxygen uptake corresponding to the value of the impulse as the measure of endurance.

2. The endurance calculation device according to claim 1, further comprising:
    a measurement unit configured to measure exercise intensity representing an intensity of exercise when the subject is walking, wherein
    the endurance calculation unit calculates, based on a value of the impulse acting on the subject when the exercise intensity measured by the measurement unit is maximized, the maximum oxygen uptake corresponding to the value of the impulse.

3. The endurance calculation device according to claim 1, further comprising:
    a measurement unit configured to measure exercise intensity representing an intensity of exercise when the subject is walking, wherein
    the endurance calculation unit calculates, based on a value of the impulse when the exercise intensity measured by the measurement unit continues to be larger than a predetermined value for a predetermined period of time, the maximum oxygen uptake corresponding to the value of the impulse.

4. The endurance calculation device according to any one of claims 2 and 3, wherein the exercise intensity includes one or more of either pulse rate, heart rate, or calorie expenditure of the subject.

5. The endurance calculation device according to claim 1, wherein when the value of the impulse calculated by the impulse calculation unit is larger than a predetermined value and maintained constant for a predetermined period of time, the endurance calculation unit calculates the maximum oxygen uptake corresponding to the value of the impulse.

6. The endurance calculation device according to claim 1, wherein the output unit alternately outputs second walking information and third walking information at predetermined timing;
    the second walking information is information prompting the subject to walk at normal speed; and
    the third walking information is information prompting the subject to walk faster than the normal speed.

7. An endurance calculation device detachably worn by a subject, comprising:
    an acceleration sensor configured to measure acceleration acting on the subject;
    an impulse calculation unit configured to calculate an impulse acting on the subject based on a value of the acceleration outputted from the acceleration sensor;
    an output unit configured to output first walking information, which is information prompting the subject to increase walking speed from low speed to maximum speed, and to alternately output second walking information, which is information prompting the subject to walk at normal speed, and third walking information, which is information prompting the subject to walk faster than the normal speed, at predetermined timing;
    an endurance calculation unit configured to calculate, based on a value of the impulse calculated by the impulse calculation unit, endurance of the subject corresponding to the value of the impulse after the first walking information is outputted by the output unit; and
    a reference value setting unit configured to set a first reference value to a certain proportion of a maximum value of the impulse calculated by the impulse calculation unit, wherein
    when the value of the impulse calculated by the impulse calculation unit is larger than the first reference value, the output unit outputs physical information representing information related to physical parameters of the subject.

8. The endurance calculation device according to claim 7, wherein the physical information is one of either proper information or improper information;
the proper information indicates that a load being applied to the subject is physically proper for the subject; and
the improper information indicates that the load being applied to the subject is not physically proper for the subject.

9. The endurance calculation device according to claim 8, wherein the reference value setting unit sets a second reference value to the maximum value of the impulse calculated by the impulse calculation unit; and
the output unit outputs the proper information when the value of the impulse calculated by the impulse calculation unit is larger than the first reference value and outputs the improper information when the value of impulse is larger than the second reference value.

10. The endurance calculation device according to claim 7, further comprising:
a reference value change unit configured to change the first reference value, when the value of the impulse calculated by the impulse calculation unit is larger than the first reference value, according to a difference between the value of the impulse and the first reference value.

11. The endurance calculation device according to claim 9, further comprising:
a reference value change unit configured to change the second reference value, when the value of the impulse calculated by the impulse calculation unit is larger than the second reference value, according to a difference between the value of the impulse and the second reference value.

12. An endurance calculation method using an endurance calculation device detachably worn by a subject, comprising:
a step of measuring acceleration acting on the subject;
a step of calculating an impulse acting on the subject based on a measured value of the acceleration;
a step of outputting first walking information, which is information prompting the subject to increase walking speed from low speed to a maximum speed; and
a calculation step of calculating, based on a value of the impulse calculated, a measure of endurance of the subject after the first walking information is outputted, wherein
in the calculation step, maximum oxygen uptake corresponding to the value of the impulse is calculated as the measure of endurance.

13. The endurance calculation method according to claim 12, further comprising:
a step of measuring exercise intensity representing an intensity of exercise when the subject is walking, wherein in the calculation step, the maximum oxygen uptake corresponding to a value of the impulse is calculated based on the value of the impulse acting on the subject when the measured exercise intensity is maximized.

14. The endurance calculation method according to claim 12, further comprising:
a step of measuring exercise intensity representing an intensity of exercise when the subject is walking, wherein
in the calculation step, the maximum oxygen uptake corresponding to a value of the impulse is calculated based on the value of the impulse when the exercise intensity measured by the measurement unit continues to be higher than a predetermined amount for a predetermined period of time.

15. The endurance calculation method according to any one of claims 13 and 14, wherein the exercise intensity includes one or more of either pulse rate, heart rate, or calorie expenditure of the subject.

16. The endurance calculation method according to claim 12, wherein in the calculation step, when the calculated value of the impulse is larger than a predetermined value and maintained constant for a predetermined period of time, the endurance of the subject corresponding to the value of the impulse is calculated.

17. The endurance calculation method according to claim 12, further comprising:
a step of alternately outputting second walking information and third walking information at predetermined timing;
the second walking information is information prompting the subject to walk at normal speed; and
the third walking information is information prompting the subject to walk faster than the normal speed.

18. An endurance calculation method using an endurance calculation device detachably worn by a subject, comprising:
a step of measuring acceleration acting on the subject;
a step of calculating an impulse acting on the subject based on a measured value of the acceleration;
a step of outputting first walking information, which is information prompting the subject to increase walking speed from low speed to a maximum speed; and
a calculation step of calculating, based on a value of the impulse calculated, a measure of endurance of the subject corresponding to the value of the impulse after the first walking information is outputted;
a step of alternately outputting second walking information, which is information prompting the subject to walk at normal speed, and third walking information, which is information prompting the subject to walk faster than the normal speed, at predetermined timing;
a step of setting a first reference value to a certain proportion of a maximum value of the calculated impulse; and
a step of outputting physical information representing information related to physical parameters of the subject when the calculated value of the impulse is larger than the first reference value.

19. The endurance calculation method according to claim 18, wherein the physical information is one of either proper information or improper information;
the proper information indicates that a load being applied to the subject is physically proper for the subject; and
the improper information indicates that the load being applied to the subject is not physically proper for the subject.

20. The endurance calculation method according to claim 19, further comprising:
a step of setting a second reference value to the maximum value of the calculated impulse, and
a step of outputting the proper information when the calculated value of the impulse is larger than the first reference value and outputs the improper information when the calculated value of the impulse is larger than the second reference value.

21. The endurance calculation method according to claim 18, further comprising:

a step of changing the first reference value, when the calculated value of the impulse is larger than the first reference value, according to a difference between the calculated value of the impulse and the first reference value.

22. The endurance calculation device according to claim 20, further comprising:
a step of changing the second reference value, when the calculated value of the impulse is larger than the second reference value, according to a difference between the calculated value of the impulse and the second reference value.

23. A computer program product executable by a computer detachably worn by a subject, the computer program product comprising a computer-readable storage medium storing at least the following computer-executable instructions:
an instruction configured to measure acceleration acting on the subject by using an acceleration sensor provided in the computer;
an instruction configured to calculate impulse acting on the subject based on a measured value of the acceleration;
an instruction configured to output first walking information, which is information prompting the subject to increase walking speed from low speed to a maximum speed, by using an output unit provided in the computer;
a calculation instruction configured to calculate, based on a value of the impulse calculated, a measure of endurance of the subject after the first walking information is outputted; and
an instruction configured to output information indicative of the measure of endurance calculated by using the output unit;
wherein the calculation instruction calculates maximum oxygen uptake corresponding to the value of the impulse as the measure of endurance.

24. The computer program product according to claim 23, further comprising:
an instruction configured to measure exercise intensity representing an intensity of exercise when the subject is walking, wherein the calculation instruction calculates, based on a value of the impulse acting on the subject when the measured exercise intensity is maximized, the maximum oxygen uptake corresponding to the value of the impulse.

25. The computer program product according to claim 23, further comprising:
an instruction configured to measure exercise intensity representing an intensity of exercise when the subject is walking, wherein the calculation instruction calculates, based on a value of the impulse when the exercise intensity measured continues to be larger than a predetermined amount for a predetermined period of time, the maximum oxygen uptake corresponding to the value of the impulse.

26. The computer program product according to any one of claims 24 and 25, wherein the exercise intensity includes one or more of either pulse rate, heart rate, or calorie expenditure of the subject.

27. The program product according to claim 23, wherein the calculation instruction calculates, when the calculated value of the impulse is higher than a predetermined value and maintained constant for a predetermined period of time, the maximum oxygen uptake corresponding to the value of the impulse.

28. The computer program product according to claim 23, further comprising:
an instruction configured to alternately output second walking information and third walking information at predetermined timing;
the second walking information is information prompting the subject to walk at normal speed; and
the third walking information is information prompting the subject to walk faster than the normal speed.

29. The program product according to claim 28, further comprising:
an instruction configured to set a first reference value to a certain proportion of a maximum value of the calculated impulse; and
an instruction configured to output physical information representing information related to physical parameters of the subject when the calculated value of the impulse is larger than the first reference value.

30. The computer program product according to claim 29, wherein
the physical information is one of either proper information or improper information;
the proper information indicates that a load being applied to the subject is physically proper for the subject; and
the improper information indicates that the load being applied to the subject is not physically proper for the subject.

31. The computer program product according to claim 30, further comprising:
an instruction configured to set a second reference value to the maximum value of the calculated impulse, and
an instruction configured to output the proper information when the calculated value of the impulse is larger than the first reference value and outputs the improper information when the calculated value of the impulse is larger than the second reference value.

32. The computer program product according to claim 29, further comprising:
an instruction configured to change the first reference value, when the calculated value of the impulse is larger than the first reference value, according to a difference between the value of the impulse and the first reference value.

33. The computer program product device according to claim 31, further comprising:
an instruction configured to change the second reference value, when the calculated value of the impulse is larger than the second reference value, according to a difference between the value of the impulse and the second reference value.

* * * * *